US00PP21359P2

(12) United States Plant Patent
Cully

(10) Patent No.: US PP21,359 P2
(45) Date of Patent: Oct. 5, 2010

(54) HYBRID OAK TREE NAMED 'TAYLOR'

(50) Latin Name: *Quercus robur×Quercus muehlenbergii×Quercus macrocarpa*
Varietal Denomination: Taylor

(76) Inventor: Earl Cully, 846 Hoagland Rd., Jacksonville, IL (US) 62650

( * ) Notice: Subject to any disclaimer, the term of this patent is extended or adjusted under 35 U.S.C. 154(b) by 35 days.

(21) Appl. No.: 12/290,077

(22) Filed: Oct. 28, 2008

(51) Int. Cl.
*A01H 5/00* (2006.01)

(52) U.S. Cl. ..... Plt./225

(58) Field of Classification Search ..... Plt./225
See application file for complete search history.

*Primary Examiner*—Susan B McCormick Ewoldt

(57) ABSTRACT

A new and distinct hybrid oak named 'Taylor' characterized by its broad, oval growth habit, glossy green mildew resistant foliage, strong wood, and rapid growth.

6 Drawing Sheets

Latin name: (*Quercus robur×Quercus muehlenbergii×Quercus macrocarpa*).

Variety denomination: 'Taylor'.

The present invention comprises a new and distinct cultivar of F2 hybrid oak tree botanically known as *Quercus robur×Quercus muehlenbergii×Quercus macrocarpa* and referred by the cultivar name 'Taylor'. The parent tree is growing in a cultivated area on the home grounds of Earl Cully, 846 Hoagland Road, eight miles southeast of Jacksonville, Ill., in Morgan County, in Township 14, Range 10. The new cultivar 'Taylor' is the result of seed collected in Mt. Hope cemetery, Urbana, Ill. in the autumn of 1974 from a *Quercus robur×Q. muehlenbergii* hybrid oak. Seed was stratified and planted in the spring of 1975. Out of this seedling progeny, two trees were selected as superior individuals. Both trees were planted at the home grounds of the inventor and one of these trees proved to be an outstanding specimen worthy of cultivar status. The selected tree grew with great vigor and was approximately forty feet in height when it was struck by lighting and killed. The tree for which this application is being made is my oldest graft which was made in the spring of 1996 and has maintained the form and hybrid vigor of the parent tree.

This hybrid is the only known cross that the inventor is aware of between these three species. The foliage of 'Taylor' is a unique combination of traits between the three species. The seed was collected from a hybrid oak between English oak (*Quercus robur*) and chinkapin oak (*Quercus muehlenbergii*). This establishes two of the three parents. The third parent is believed to be bur oak (*Quercus macrocarpa*) because the foliage is much larger in length and width than either an English oak or a chinkapin oak. Also many leaves of the 'Taylor' oak display a rounded apex with shallow lobes similar to most bur oak leaves. In addition to similarities between the foliage of 'Taylor' and *Quercus macrocarpa*, the acorn cap margin of 'Taylor' displays some short fringe hairs which are indicative of bur oak.

The 'Taylor' cultivar displays a broad-oval crown form and extremely glossy dark green leaves (FIG. 1). The foliage of the 'Taylor' oak displays high resistance to powdery mildew. The branching angle for most of the branches varies from 30 to 60 degrees giving good angle of branching (FIG. 2). The broad-oval crown form of the 'Taylor' cultivar lends itself to park and shade tree plantings in large yards or even industrial areas. The parent tree is very resistant to ice and wind damage and has come through several storms without breakage of any branches indicating very strong branching and wood structure. It is hardy in Zone 5B (U.S.D.A. Hardiness Zone Map) where it has been tested, and it may even be hardy into zone 4A considering that bur oak (hardy into zone 3B) is one of the parent species.

This cultivar has been successfully propagated by chip bud grafting onto swamp white oak (*Quercus bicolor*) understock, and cleft grafting has also been used to successfully propagate the 'Taylor' cultivar. Graft incompatibility has not been observed by the inventor between the 'Taylor' cultivar and *Quercus bicolor* understock. Chip bud propagation has produced approximately 5 feet (1.52 m) of growth in one season on two year old swamp white oak understock. Asexual propagation has been performed in a cultivated field at the inventor's home residence at 846 Hoagland road, Jacksonville, Ill. 62650 and at a wholesale nursery near Dayton, Oreg. The growth form, leaves, and fruit of asexually propagated 'Taylor' clones are identical to the original tree (FIG. 3).

The 'Taylor' oak exhibits remarkable hybrid vigor. At fourteen years of age, it has reached a height of twenty eight feet with a crown spread of twenty four feet with an average growth rate of two feet per year. The broad-oval crown, dark glossy green leaves, powdery mildew resistance of the foliage, strength, hardiness, and hybrid vigor make 'Taylor' a desirable street tree and a handsome lawn tree (FIG. 4).

DETAILED BOTANICAL DESCRIPTION

In the following description, color references are made to The Royal Horticultural Society Colour Chart.

BRIEF DESCRIPTION OF THE DRAWINGS

The accompanying colored photographs illustrate the appearance and color of the new 'Taylor' cultivar oak tree. These photographs show the color as is reasonably possible to obtain in colored reproductions of this type. Actual foliage colors may differ slightly due to light reflectance.

THE PLANT

TREE, HYBRID OAK

Figure 1:
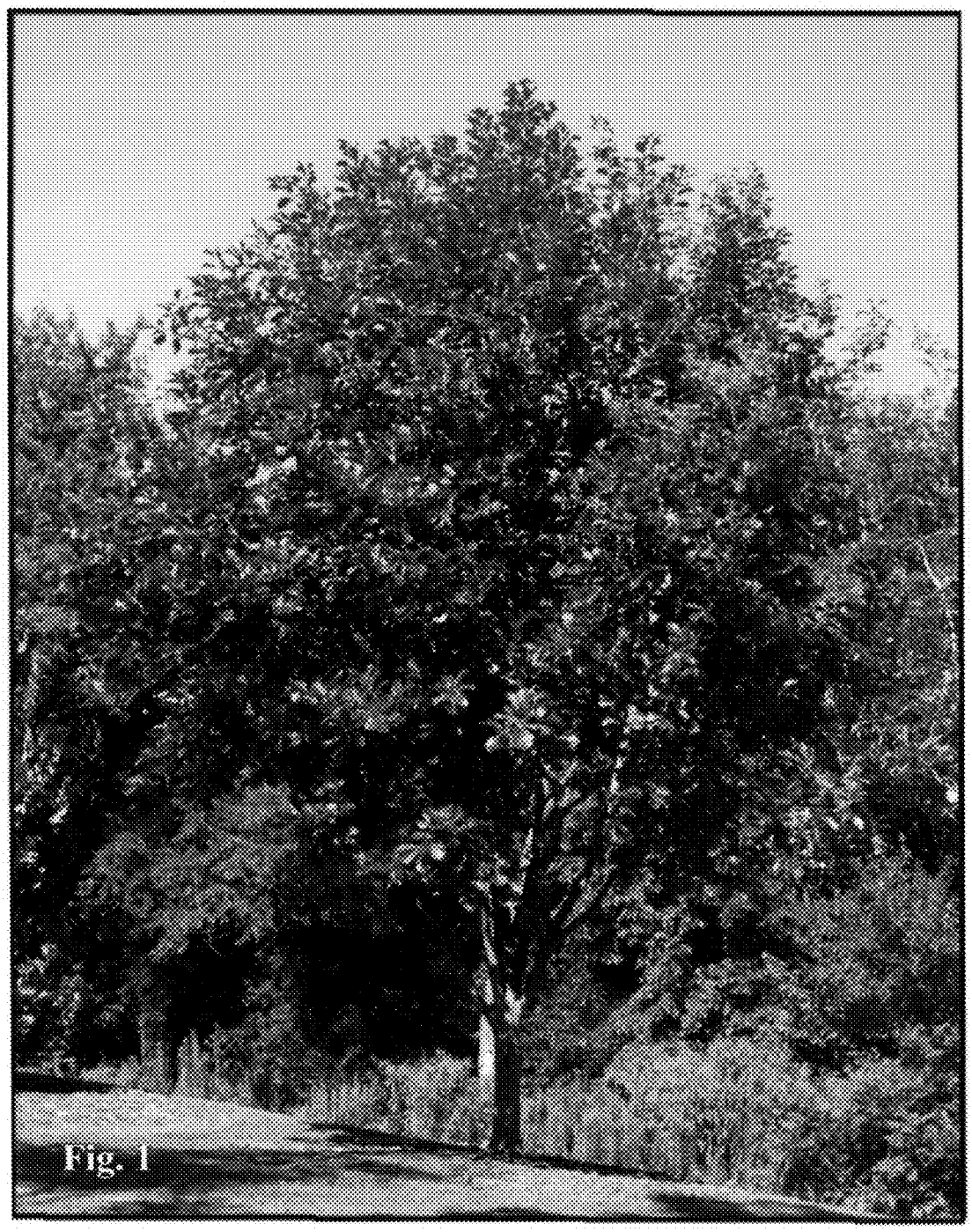
FIG. 1 depicts the initially discovered tree named 'Taylor' in summer foliage showing its broad, oval crown form and highly glossy, disease and powdery mildew free green foliage.
Figure 2:
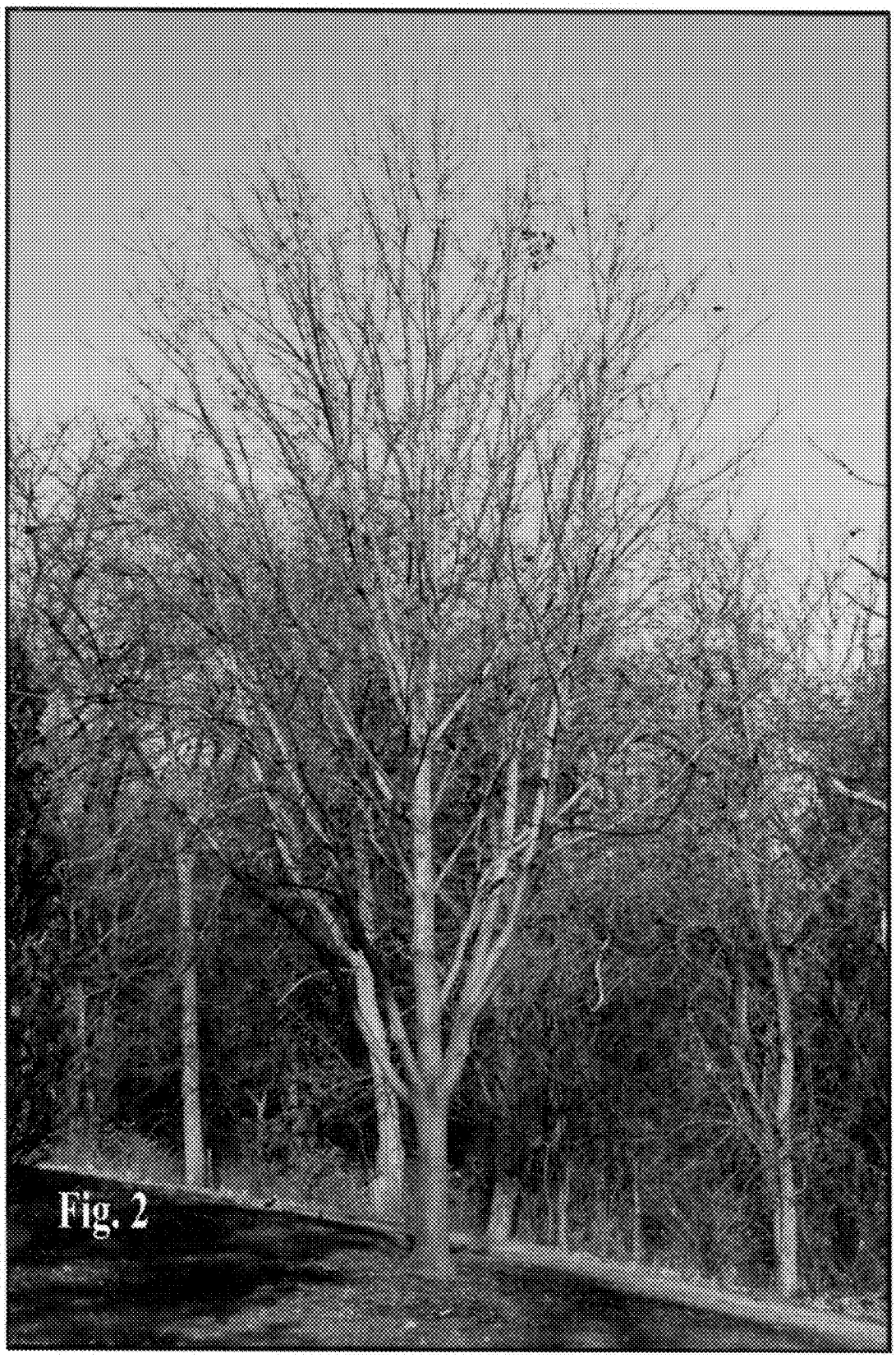
FIG. 2 depicts the 'Taylor' cultivar without foliage; thus, revealing its branching structure.
Figure 3:
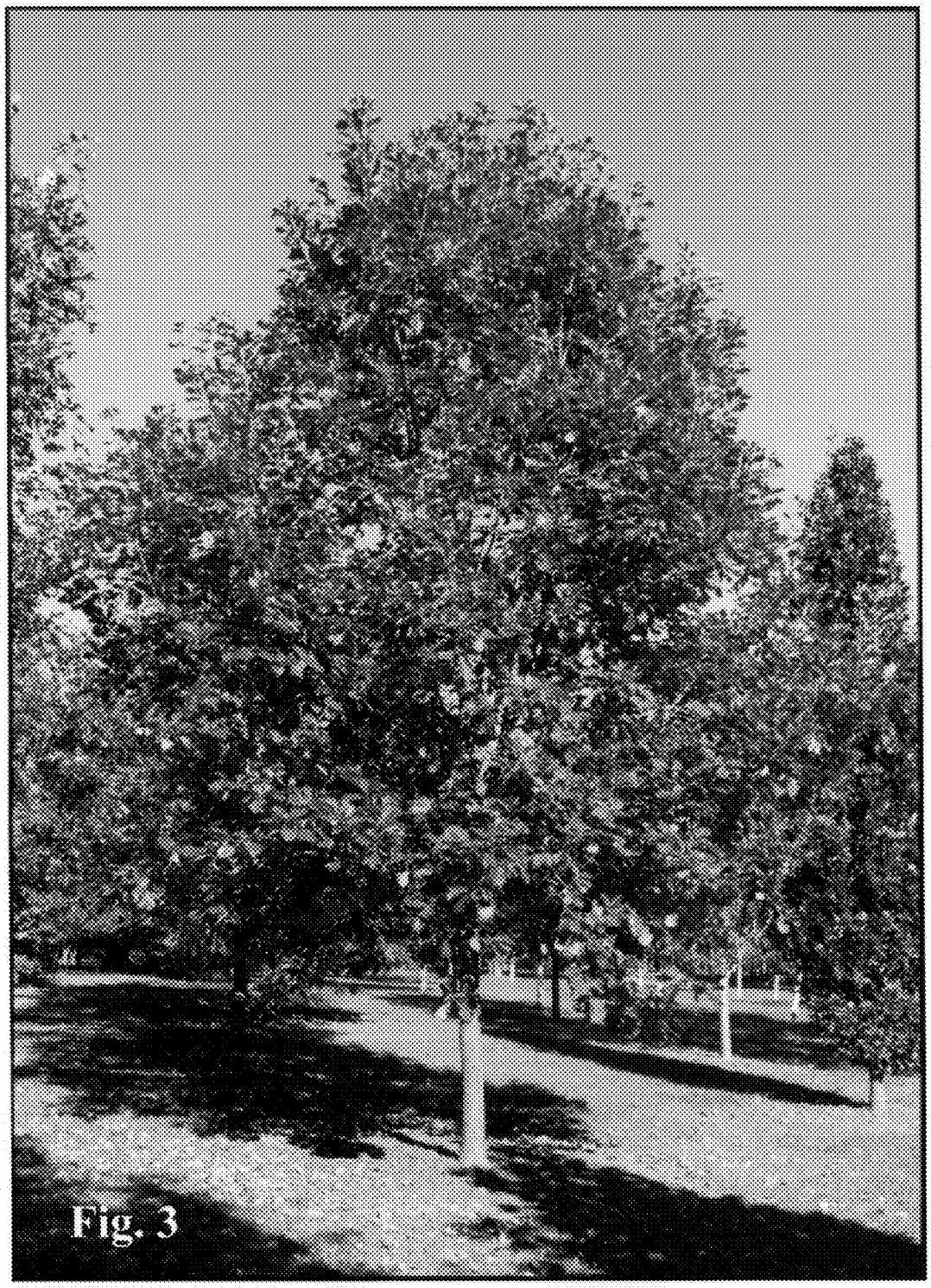
FIG. 3 depicts a clone of the 'Taylor' cultivar illustrating the same broad, oval crown from as the parent tree.
Figure 4:
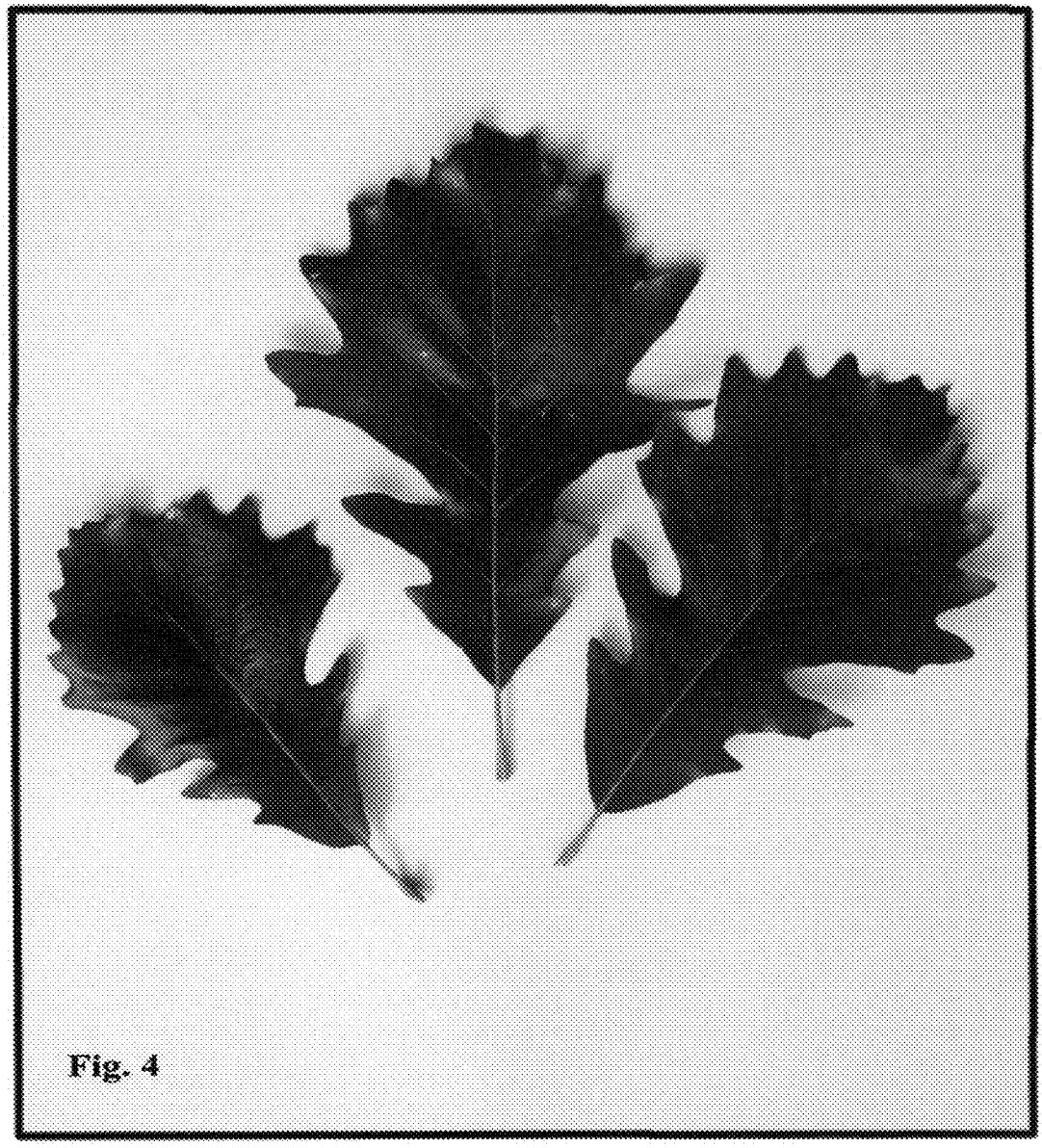
FIG. 4 depicts the powdery mildew resistant glossy foliage of the 'Taylor' oak.
Figure 5:
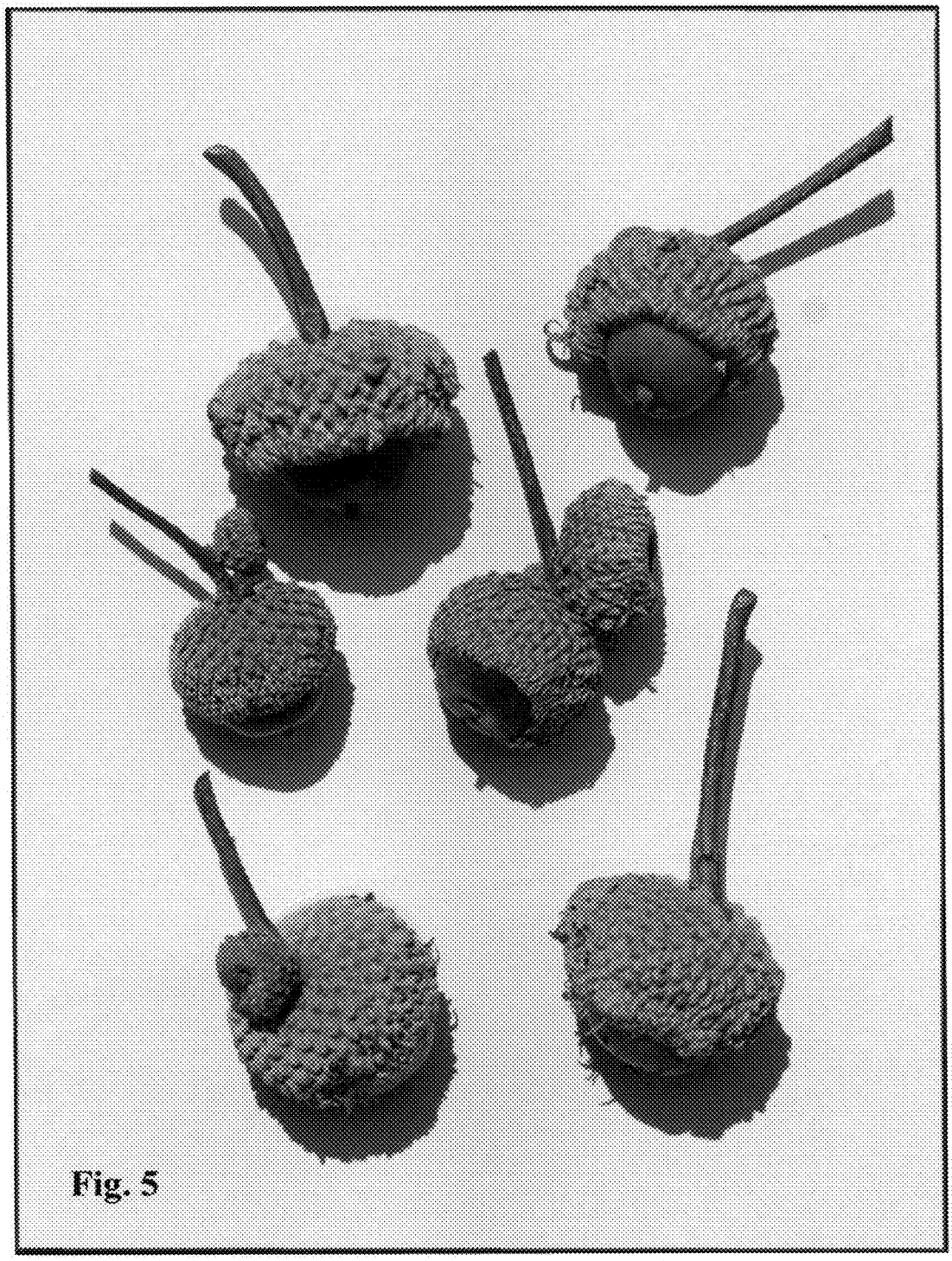
FIG. 5 depicts both mature (brown) and some immature (green) acorns of the 'Taylor' cultivar in early autumn.
Figure 6:
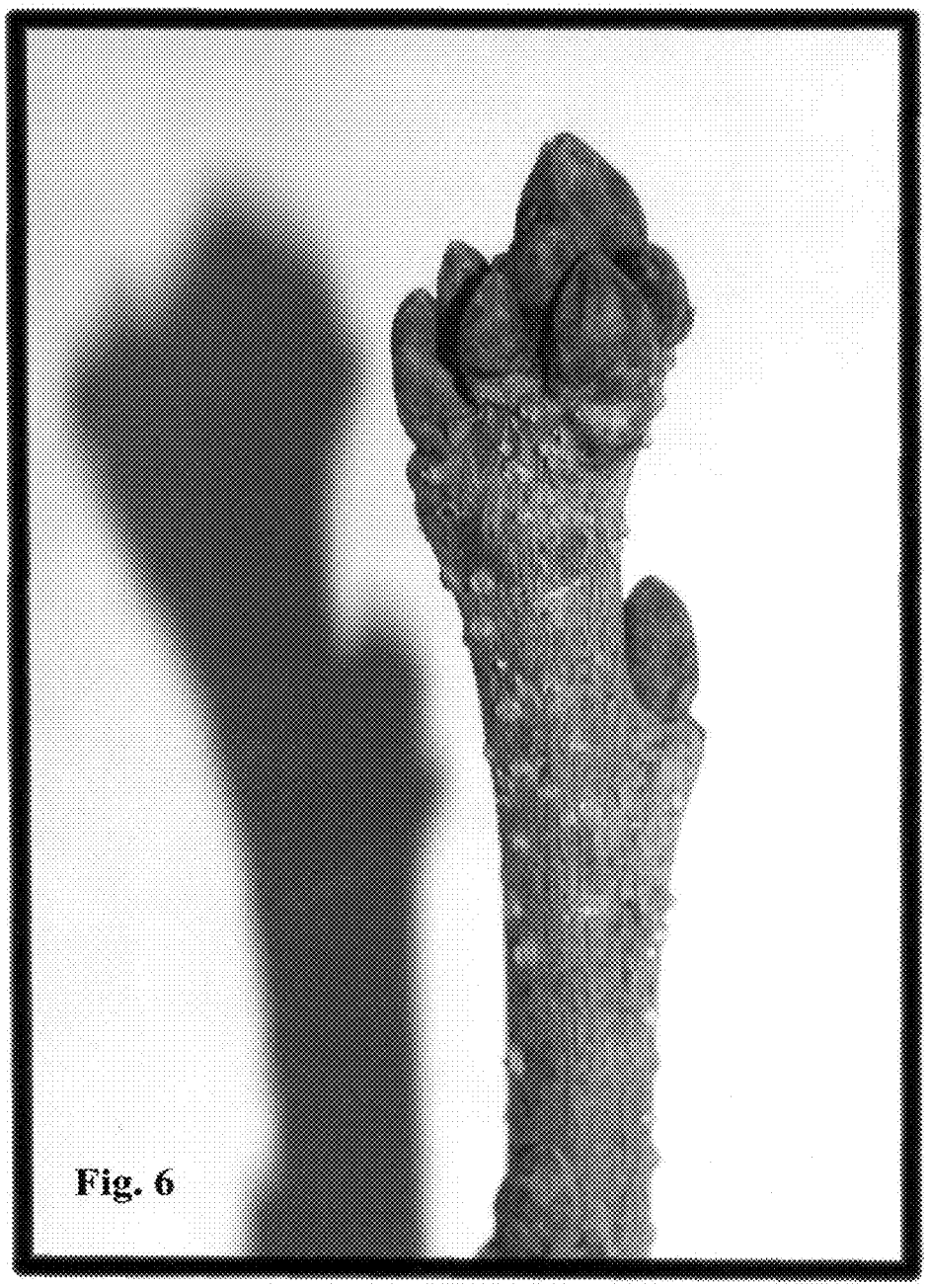
FIG. 6 depicts a twig, including terminal and lateral buds of the 'Taylor' oak.

Name: Cultivar 'Taylor'.

Parentage:

*Seedling or sport.*—Seedling.

*Seed parent.*—*Quercus robur*×*Quercus muehlenbergii.*

*Pollen parent.*—*Quercus muehlenbergii*×*Quercus macrocarpa.*

Classification: (*Quercus robur*×*Quercus muehlenbergii*)×(*Quercus muehlenbergii*×*Quercus macrocarpa*).

Discovered: This seedling was selected from a row of seedlings in a cultivated area at the home of Earl Cully located at 846 Hoagland Road, Jacksonville, Ill. 62650, Morgan County, Township 14, Range 10. Presently, the tree is being propagated by chip budding or grafting onto two-year old swamp white oak (*Quercus bicolor*) seedlings at 846 Hoagland Road, Jacksonville, Ill. 62650 and at a wholesale nursery near Dayton, Oreg.

Form: Tree.

Shape: Broad oval.

Height: 8.53 meters, 28 feet.

Spread: 7.2 meters, 23 feet 8 inches.

Trunk size: Diameter at 1.37 meters above ground 22.3 cm, 8.8 inches.

Trunk base shape: Cylindrical.

Trunk surface texture: Moderately rough, bark has vertical furrows with flat ridges.

Growth rate: Moderate to fast.

Strength: Excellent, no evidence of breakage.

Age: 14.

Bark: Furrowed vertically, breaking into short, flat plates that are longer than wide.

*Alignment of pattern.*—Vertical.

*Texture of bark.*—Moderately rough.

*Exfoliation.*—Minimal exfoliation only seen on smaller branches less than 6.4 cm in diameter.

*Size of bark pattern.*—Plates (10.2-2.5 cm) average=5.5 cm long by (1.6-1.0 cm) average=1.3 cm wide.

Branches:

*Angle of attachment.*—Most branches varied between 30°-60°, with some upper branches at 20°.

*Spacing of branches.*—Moderately dense approximately 32 cm between whorls of branches.

*Bark color.*—Grey (201A, B, and C) with some white (156D and C).

*Bark texture.*—Rough, furrowed with flattened ridges broken into plates.

*Bark exfoliation.*—Some small amounts of exfoliated bark was present on branches ≦ 2.5 cm in diameter.

*Small twig bark.*—(<0.7 cm diameter) (growing season) grey-green (197A,198B,199B) (dormant season) grey (201A) and grey-green (197A).

*Twig texture.*—Smooth overall but has small, warty lenticels.

*Lenticels.*—Small (0.05-0.11 cm), average=0.09 cm, round to oval grey-yellow (161D) to grey-orange (164D).

*Buds.*—Small triangular in shape (0.16 cm-0.48 cm), average=0.35 cm, scaled with some stiple hairs at terminal bud. Scale color varies from grey-orange (175B) at base of bud to grey-orange (176A) at tip of bud and grey-orange (177A) at edge of scale. The bud scales were arranged in an imbricate pattern with some short pubescent grey-white (156C) hairs on the scales.

Leaves:

*Petiole.*—Length: (0.6-3.5 cm), average=1.7 cm. Color: yellow-green (146D & 144C). Texture: smooth with some pubescent hairs, no warts present.

*Lamina.*—Length: (8.3 cm-22.2 cm), average=14.3 cm. Width: (4.8 cm-16.0 cm), average=9.3 cm. Form: lamina obovate to oblanceolate. Shape of lamina base: cuneate with some examples acute. Shape of lamina apex: rounded to obtuse. Margin: lobed to crenate at apex of lamina. Texture: membranous, glossy, smooth above and pubescent below. Quantity: abundant. Color: summer (upper) green (139A) (lower) green (133D) autumnal (upper) grey-orange (165A&B) (lower) grey-brown (199B,C&D). Ribs and veins: 11 to 12 pairs of prominent veins yellow-green (146C and 144C); pinnate pattern of venation.

Flowers: Imperfect, monoecious; staminate catkins are pendulous, clustered, length (3.0 cm-4.8 cm), average=4.4 cm yellow-green (154B); pistillate flowers are found in the axils of the emerging new leaves, ovary surrounded by a calyx 0.1-0.3 cm in length, color yellow-green (154B).

Fruit: Nut (acorn), acorn color of mature acorn is brown (200B&C), length (cap and acorn) (2.86 cm-3.81 cm) average=3.29, cap width (3.2 cm-2.54 cm) average=2.8 cm; length of the acorn (3.2 cm-2.2 cm) average=2.4 cm; cap length (2.2 cm-1.9 cm) average=2.1 cm; cap depth (2.0 cm-1.6 cm) average=1.8 cm; mature cap color is grey-brown (197B&C), immature cap color is a mixture of yellow-green (147C and 143C); imbricate scales on cap have a rough, warty texture, a ring of sparse, short hairs fringe the bottom of the cap; inside, the cap is pubescent; cap encloses 66% to 50% of the acorn.

Has this plant ever been offered for sale? No.

Compare this new variety with others of the same species and with its parent or parents; state the distinguishing characteristics of the new cultivar and its advantages.

The 'Taylor' cultivar differs from its parents in having foliage that is a unique combination of traits from all three parents. The tree displays hybrid vigor and rapidly forms a broad-oval crown within fourteen years of asexual propagation. Seedling English oak, chinkapin oak, and bur oak tend to form a pyramidal crown in youth and only develop a broad crown with age. No other oak cultivars would come close to having the same characteristics as the 'Taylor' cultivar. 'Taylor' has larger foliage than 'Clemons' cultivar U.S. Plant Pat. No. 11,431 even though they share similar parents in English oak and bur oak. 'Taylor' also develops a broad-oval crown in youth while 'Clemons' has a broad pyramidal crown form that becomes broad-oval after 30-40 years of growth. 'Taylor' also shares a parent species (*Quercus robur*) with the 'Long' cultivar U.S. Plant Pat. No. 12,673 and the 'Nadler' cultivar U.S. Plant Pat. No. 17,604, but 'Taylor' differs in its broad-oval form from the medium oval form of 'Long' and the narrow columnar form of 'Nadler'. Both 'Long' and 'Nadler' have a white underside to their foliage, but the 'Taylor' foliage has a light green underside.

It is claimed:

1. A new and distinct cultivar of hybrid oak tree (*Quercus*× *muehlenbergii*×*Quercus robur*×*Quercus macrocarpa*) as herein described and illustrated.

* * * * *